(12) United States Patent
Hixon (10) Patent No.: US 8,644,666 B2
(45) Date of Patent: Feb. 4, 2014

(54) METHODS AND APPARATUS RELATED TO AN OPTICAL FIBER MEMBER HAVING A REMOVABLE COVER

(71) Applicant: Boston Scientific Scimed, Inc., Maple Grove, MN (US)

(72) Inventor: Jessica Hixon, Brighton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/962,235

(22) Filed: Aug. 8, 2013

(65) Prior Publication Data

US 2013/0324799 A1 Dec. 5, 2013

Related U.S. Application Data

(63) Continuation of application No. 12/958,851, filed on Dec. 2, 2010, now Pat. No. 8,532,456.

(60) Provisional application No. 61/287,458, filed on Dec. 17, 2009.

(51) Int. Cl.
*G02B 6/036* (2006.01)
*A61B 1/06* (2006.01)

(52) U.S. Cl.
USPC ............................. 385/128; 362/574; 600/182

(58) Field of Classification Search
None
See application file for complete search history.

(56) References Cited

U.S. PATENT DOCUMENTS

| | | | |
|---|---|---|---|
| 4,740,047 | A | 4/1988 | Abe et al. |
| 5,257,991 | A | 11/1993 | Fletcher et al. |
| 5,343,543 | A | 8/1994 | Novak, Jr. et al. |
| 5,357,955 | A | 10/1994 | Wolf et al. |
| 5,638,483 | A | 6/1997 | Konwitz |
| 5,772,657 | A | 6/1998 | Hmelar et al. |
| 6,296,608 | B1 | 10/2001 | Daniels et al. |
| 6,615,072 | B1 | 9/2003 | Izatt et al. |
| 6,928,202 | B2 | 8/2005 | Pickrell et al. |
| 7,169,140 | B1 | 1/2007 | Kume |
| 7,207,980 | B2 | 4/2007 | Christian et al. |
| 2005/0203419 | A1 | 9/2005 | Ramanujam et al. |
| 2006/0078265 | A1 | 4/2006 | Loeb |
| 2007/0179485 | A1 | 8/2007 | Yeik et al. |
| 2009/0180745 | A1 | 7/2009 | Zerfas et al. |
| 2010/0016845 | A1 | 1/2010 | Hanley et al. |
| 2010/0198009 | A1 | 8/2010 | Farr et al. |

*Primary Examiner* — Jerry Rahll
(74) *Attorney, Agent, or Firm* — Bookoff McAndrews, PLLC (57) ABSTRACT

An apparatus may include a waveguide. The waveguide may include a distal end surface which may be substantially normal to a centerline of a distal end portion of the waveguide. The apparatus may further include a cover which may be coupled to a portion of the waveguide. The cover may include a portion distal to the distal end surface of the waveguide, and the portion of the cover may be made of a material which may be configured to be removed when exposed to electromagnetic radiation emitted from a portion of the distal end surface of the waveguide.

20 Claims, 6 Drawing Sheets

METHODS AND APPARATUS RELATED TO AN OPTICAL FIBER MEMBER HAVING A REMOVABLE COVER

CROSS REFERENCE TO RELATED APPLICATION

This application is a continuation of U.S. patent application Ser. No. 12/958,851, filed Dec. 2, 2010, which claims the benefit of priority under 35 U.S.C. §119 to U.S. Provisional Patent Application No. 61/287,458, filed Dec. 17, 2009, both of which are incorporated herein by reference.

FIELD OF THE INVENTION

Embodiments relate generally to optical medical devices, and, in particular, to a cover for an optical fiber member and methods for using such devices.

BACKGROUND OF THE INVENTION

During a ureteroscopy procedure, a medical practitioner can insert an endoscope (such as a ureteroscope) into a patient's urinary tract, for example, over a guide wire to locate an undesirable object such as a kidney stone or a bladder stone. Once the stone is located, an optical fiber member can be introduced into a working channel of the endoscope and advanced within the working channel until the optical fiber comes into contact with or in close proximity to the stone. Electromagnetic radiation from, for example, an electromagnetic radiation source (e.g., a holmium (Ho) laser source) can be directed through a waveguide of the optical fiber member towards the stone to break the stone into fragments. The fragments can be removed with, for example, a basket tool via the working channel or flushed through normal urinary activity. This type of ureteroscopy procedure, which can be minimally invasive, can be performed under, for example, a general anesthetic.

Many known optical fiber members that are used in ureteroscopy procedures have, for example, cleaved distal ends with edges that can be relatively sharp. The distal end edge of a known optical fiber member can snag on and/or cut into an inner surface (e.g., an inner liner) of a working channel of an endoscope as the optical fiber member is advanced within the working channel during a ureteroscopy procedure. A snag can result, for example, in an undesirable delay during a ureteroscopy procedure and/or in damage (e.g., irreparable harm) to the endoscope. The potential for the distal end of a known optical fiber member to snag or cut a working channel of an endoscope is particularly high when the optical fiber member is advanced through a portion of the working channel that is intentionally or unintentionally bent during a ureteroscopy procedure. Thus, a need exists for a cover coupled to a distal end portion of an optical fiber member that can address at least some of these issues.

SUMMARY OF THE INVENTION

An aspect of the present disclosure may include an apparatus having a waveguide. The waveguide may include a distal end surface which may be substantially normal to a centerline of a distal end portion of the waveguide. The apparatus may further include a cover which may be coupled to a portion of the waveguide. The cover may include a portion distal to the distal end surface of the waveguide, and the portion of the cover may be made of a material which may be configured to be removed when exposed to electromagnetic radiation emitted from a portion of the distal end surface of the waveguide.

Various embodiments of the disclosure may include one or more of the following aspects: the portion of the cover may be coupled to the distal end surface of the waveguide; the cover may be coupled to an edge of the distal end surface of the waveguide; the waveguide may further comprise a cladding layer, and the edge of the distal end surface of the waveguide may be substantially defined by the cladding layer of the waveguide; the cover may include a substantially spherical shape; the cover may include a toroid shape that may define an opening substantially aligned along a plane normal to a centerline of a fiber core of the distal end portion of the waveguide; the material may be substantially opaque to the electromagnetic radiation when emitted from the distal end surface of the waveguide; a jacket may be disposed around the waveguide proximally to the portion of the cover, and the material of the portion of the cover may include a composition substantially similar to a composition of the jacket; a jacket may be disposed around the waveguide, and the cover may be coupled to a portion of the jacket; a jacket may be disposed around the waveguide, and the cover may include a proximal end separated from a distal end of the jacket by an air gap; the distal end surface of the waveguide may be defined partially by a fiber core of the waveguide; the cover may be adhesively coupled to at least one of a cladding layer of the waveguide and the portion of the edge; and the waveguide may be included in a ureteroscope.

An aspect of the present disclosure may include a method including removing a portion of a jacket disposed on a waveguide such that an axial portion of a cladding layer of the waveguide may be exposed. A distal end surface of the waveguide may be defined by the cladding layer and a fiber core of the waveguide, and the distal end surface of the waveguide may be substantially normal to a centerline of the waveguide. The method may further include disposing a material on an edge of the distal end surface and on a portion of the distal end surface of the waveguide. The material may be configured to be removed when exposed to electromagnetic radiation emitted from a portion of the distal end surface of the waveguide.

Various embodiments of the disclosure may include one or more of the following aspects: the disposing step may include disposing the material on a portion of the axial portion of the cladding layer; removing a first portion of the material such that a second portion of the material remaining on the edge of the distal end surface may have an arc of curvature co-planar with the centerline of the waveguide; the disposing step may be performed using at least one of a dipping process and a deposition process; and the method may also include defining a cover having a cavity defined by an inner surface of the cover, wherein the material may define a portion of the inner surface of the cover, and the disposing step may include moving the portion of the inner surface over the waveguide.

An aspect of the present disclosure may include a method comprising inserting a distal end portion of a waveguide into a body of a patient through an endoscopic tube. The waveguide may include a removable material coupled to a distal end surface of the distal end portion of the waveguide, and the distal end surface may be substantially normal to a centerline of the distal end portion of the waveguide. The method may further include activating an electromagnetic radiation source coupled to a proximal end portion of the waveguide such that a portion of the removable material may be removed from the distal end surface by electromagnetic radiation emitted from the electromagnetic radiation source.

Various embodiments of the disclosure may include the following aspect: the removable material may be configured such that the portion of the removable material may be removed within one second of the activating.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the present embodiments, examples of which are illustrated in the accompanying drawings. Wherever possible, the same reference numbers will be used throughout the drawings to refer to the same or like parts.

The devices and methods described herein are generally related to an optical fiber member configured to treat a target treatment area within a body of a patient. Specifically, the optical fiber member can be used to transmit electromagnetic radiation (e.g., laser energy) from an electromagnetic radiation source (e.g., a laser energy source) to the target treatment area when at least a portion of the optical fiber member is disposed within, for example, an endoscope. The electromagnetic radiation can be transmitted into and/or propagated within a waveguide of the optical fiber member. In some embodiments, the waveguide can be referred to as an optical waveguide. A proximal end portion of the optical fiber member can be coupled to the electromagnetic radiation source while the distal end portion of the optical fiber member can be inserted into the patient's body to provide the electromagnetic radiation treatment. In some embodiments, the waveguide of the optical fiber member can include, for example, a fiber core, one or more cladding layers disposed around the fiber core, and/or so forth. In some embodiments, the optical fiber member can also have a buffer layer disposed around the cladding layer(s) and/or a jacket (e.g., a jacket layer disposed around the buffer layer). The jacket can also be referred to as a jacket coating, and the buffer layer can be referred to as a buffer coating.

A distal end portion of the optical fiber member can have a cover configured so that the optical fiber member can be moved (e.g., advanced), for example, within a lumen (e.g., an endoscopic lumen or working channel) without snagging on an inner surface of the lumen. Specifically, the cover can have a smooth surface and can be coupled to the distal end portion of the optical fiber member so that the optical fiber member can be slidably moved within the lumen during placement (e.g., insertion) of at least a portion of the optical fiber member in a body of a patient (e.g., in close proximity to a target treatment area within a body of a patient). Placement of the optical fiber member can be performed during a placement portion (also can be referred to as an insertion portion) of a medical procedure.

The cover can be made of a material configured to be removed (e.g., detached, separated, fragmented, broken-up, pulverized, disintegrated, burned back, ablated) when exposed to electromagnetic radiation emitted from at least a portion of the distal end of the optical fiber member. The cover can be made of a removable material so that after the optical fiber member has been placed in a desirable position, the cover can be removed (e.g., removed using electromagnetic radiation) from a portion of the optical fiber member used for treatment of the patient. In other words, the cover can be removed so that electromagnetic radiation can be emitted from a waveguide of the optical fiber member towards a target treatment area without being blocked by the cover. The cover can be removed during a removal portion of a medical procedure, and the patient can be treated using the optical fiber member during a treatment portion of the medical procedure. In some embodiments, a cover made of a removable material can be referred to as a removable cover.

In some embodiments, the cover can be coupled to the optical fiber member after at least a portion of a jacket of the optical fiber member has been removed to expose at least a portion of the waveguide of the optical fiber member (e.g., a portion of a cladding layer of the optical fiber member). For example, the cover can be coupled to a distal end surface (e.g., a cleaved distal end surface) of a waveguide of the optical fiber member, a cladding layer disposed circumferentially (e.g., axially) around at least a portion of an optical fiber member, and/or a jacket of the optical fiber member.

In some embodiments, the devices and methods described herein can be used in treating symptoms related to, for example, a kidney stone and/or an enlarged prostate gland, a condition known as Benign Prostatic Hyperplasia (BPH). Specifically, electromagnetic radiation from a holmium:YAG (Ho:YAG) electromagnetic radiation source can be propagated through the optical fiber member to remove the kidney stone and/or the obstructive prostate tissue. The Ho:YAG surgical electromagnetic radiation source is a solid-state, pulsed electromagnetic radiation source that emits light at a wavelength of approximately 2100 nanometers (nm). This wavelength of light is particularly useful for, for example, tissue ablation because it is strongly absorbed by water. An advantage of Ho:YAG electromagnetic radiation sources is that they can be used for both tissue cutting and for coagulation.

It is noted that, as used in this written description and the appended claims, the singular forms "a," "an" and "the" include plural referents unless the context clearly dictates otherwise. Thus, for example, the term "a wavelength" is intended to mean a single wavelength or a combination of wavelengths. Furthermore, the words "proximal" and "distal" refer to direction closer to and away from, respectively, an operator (e.g., a medical practitioner, a nurse, a technician, etc.) who would insert a medical device into a patient. Thus, for example, an end of an optical fiber member inserted inside a patient's body would be the distal end of the optical fiber member, while an end of the optical fiber member outside of a patient's body would be the proximal end of the optical fiber member.

Figure 1A:
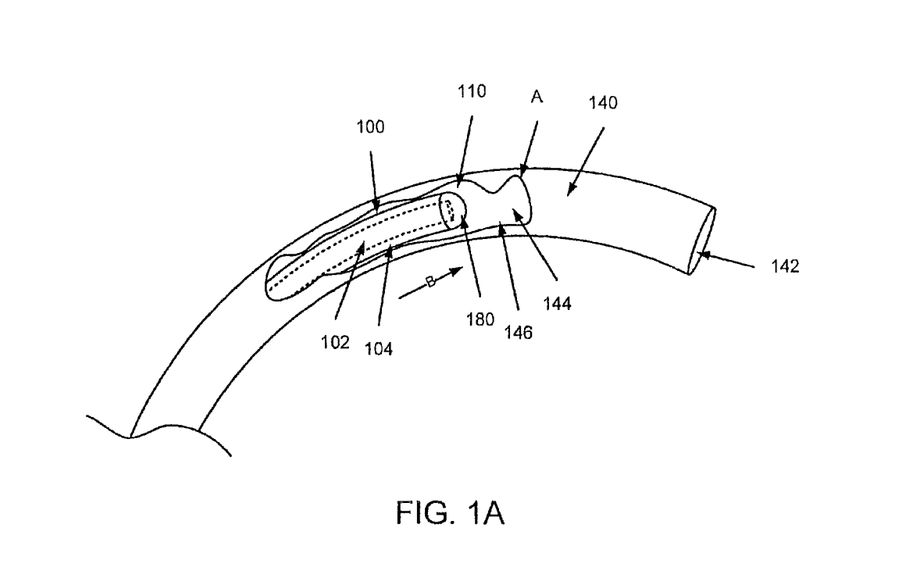
FIG. 1A is a schematic diagram that illustrates a side view of a distal end portion of an optical fiber member disposed within a lumen defined by an endoscopic tube, according to an embodiment.

FIG. 1A is a schematic diagram that illustrates a side view of a distal end portion 110 of an optical fiber member 100 disposed within a lumen 144 defined by an endoscopic tube 140, according to an embodiment. As shown in FIG. 1 through cut-away A in the endoscopic tube 140, the optical fiber member 100 includes a waveguide 102, a jacket 104, and a cover 180. As shown in FIG. 1A, the jacket 104 (e.g., a polymer-based jacket, a Tefzel® jacket) can be disposed around the waveguide 102 of the optical fiber member 100.

The cover 180 is defined so that the distal end portion 110 of the optical fiber 100 can be moved (e.g., advanced), for example, in a distal direction B within the lumen 144 without snagging on an inner surface 146 that defines the lumen 144 of the endoscopic tube 140. Specifically, the cover 180 can have a relatively smooth outer surface configured to slide along the inner surface 146 of the endoscopic tube 140 when the optical fiber member 100 is moved within the endoscopic tube 140. In some embodiments, the inner surface 146 of the endoscopic tube 140 can be associated with an integral inner liner (not shown) or a separate inner liner (not shown).

In some embodiments, the cover 180 can have a shape defined so that the optical fiber member 100 can be moved in a proximal direction (not shown) substantially opposite the distal direction B without, for example, snagging on the inner surface 146 that defines the lumen 144 of the endoscopic tube 140. In some embodiments, an outer diameter of the cover 180 can be equal to or greater than an outer diameter of the jacket 104. In some embodiments, an outer diameter of the cover 180 can be smaller than an outer diameter of the jacket 104.

The waveguide 102 of the optical fiber member 100 can be disposed within, and substantially along, an entire length of the optical fiber member 100. In some embodiments, the waveguide 102 of the optical fiber member 100 can include, for example, a fiber core, one or more buffer layers, and/or one or more cladding layers (not shown in FIG. 1A or FIG. 1B).

In some embodiments, any portion of the waveguide 102, such as a fiber core of the waveguide 102, can be made of a suitable material for the transmission of electromagnetic radiation from an electromagnetic radiation source (not shown). In some embodiments, the optical fiber member 100 can be a silica-based optical fiber member. For example, a fiber core included in the waveguide 102 can be a pure silica fiber core, and a cladding layer in the waveguide 102 and disposed around the fiber core can be a doped-silica cladding layer. In some embodiments, for example, the fiber core can be made of silica with a low hydroxyl (OW) ion residual concentration. Electromagnetic radiation wavelengths between about 500 nm to about 2100 nm can be propagated within the fiber core of the optical fiber member 100 during a surgical procedure. An example of low hydroxyl (low-OH$^-$) fibers used in medical devices is described in U.S. Pat. No. 7,169,140 to Kume, the disclosure of which is incorporated herein by reference in its entirety. The fiber core can be a multi-mode fiber core and can have a step or graded index profile. In some embodiments, electromagnetic radiation can be transmitted into (e.g., launched into) the fiber core from an electromagnetic radiation source via a connector (e.g., a launch connector) such as that described in U.S. Patent Application Publication No. US 2009/0180745 A1, filed Dec. 19, 2008, entitled "Methods and Apparatus Related to a Launch Connector Portion of a Ureteroscope Laser-Energy-Delivery Device," which is incorporated by reference herein in its entirety.

In some embodiments, any portion of the waveguide 102 (e.g., a cladding layer of the waveguide 102) can be doped with a dopant (e.g., a fluorine dopant, a chlorine dopant, a rare-earth dopant, an alkali-metal dopant, an alkali-metal-oxide dopant, an amplifying dopant, etc.). In some embodiments, a cladding layer of the waveguide 102 (if including a cladding layer) can be a single cladding or a double cladding that can be made of a hard polymer or a silica. A buffer layer of the waveguide 102 (if including a buffer layer) can be made of a relatively hard polymer such as Tefzel®.

In some embodiments, the lumen 144 of the endoscopic tube 140 can also be configured to receive various medical devices or tools, such as, for example, irrigation and/or suction devices, forceps, drills, snares, needles, etc. In some embodiments, the endoscopic tube 140 can define one or more lumens, in addition to lumen 144, through which one or more medical devices can be received. An example of such an endoscopic tube 140 with multiple lumens is described in U.S. Pat. No. 6,296,608 to Daniels et al., the disclosure of which is incorporated herein by reference in its entirety. In some embodiments, a fluid channel (not shown) can be defined by the endoscopic tube 140 and coupled at a proximal end to a fluid source (not shown). The fluid channel can be used to irrigate an interior of the patient's body during a laser-based surgical procedure. In some embodiments, an eyepiece (not shown) can be coupled to a proximal end portion of the endoscopic tube 140, for example, and coupled to a proximal end portion of an optical fiber member (separate from optical fiber member 100, not shown) that can be disposed within a lumen (e.g., lumen 144) of the endoscopic tube 140. Such an embodiment can allow a medical practitioner to view the interior of a patient's body through the eyepiece.

Figure 1B:
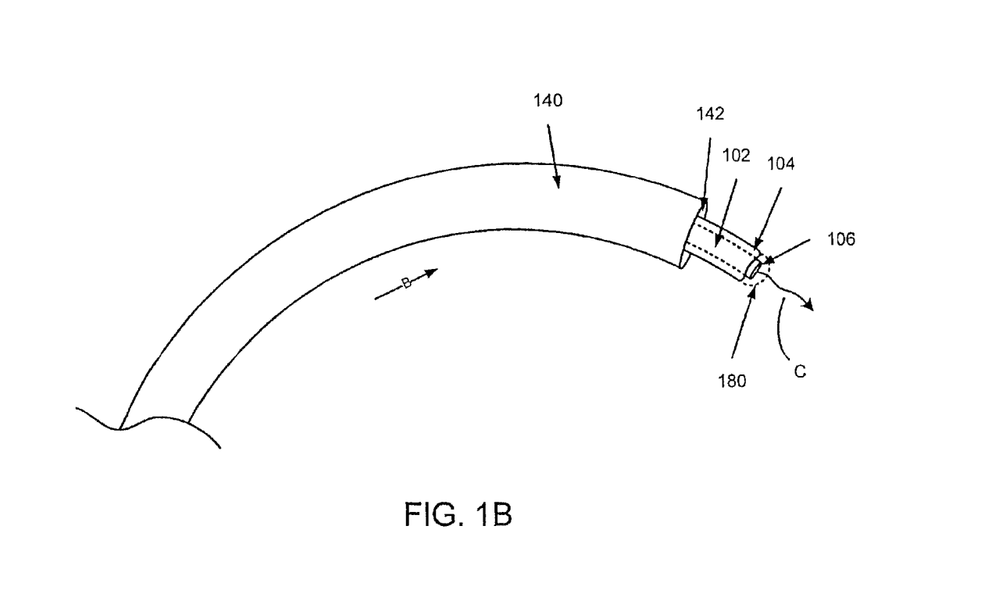
FIG. 1B is a schematic diagram that illustrates a side view of the distal end portion of the optical fiber member when disposed outside of the lumen defined by the endoscopic tube shown in FIG. 1A.

FIG. 1B is a schematic diagram that illustrates a side view of the distal end portion 110 of the optical fiber member 100 when disposed outside of the lumen 144 defined by the endoscopic tube 140 shown in FIG. 1A. The distal end portion 110 of the optical fiber member 100 can be moved from the position disposed inside of the lumen 144 (shown in FIG. 1A) to the position disposed outside of the lumen 144 (shown in FIG. 1B) via opening 142 defined by the endoscopic tube 140. In some embodiments, the distal end portion 110 of the optical fiber member 100 can be moved (e.g., slidably moved) from the position disposed within the lumen 144 to the position disposed outside of the lumen 144 after at least a portion of the endoscopic tube 140 has been disposed within a body of a patient (not shown). In such instances, the distal end portion 110 of the optical fiber member 100 can be moved into the body of the patient when being moved outside of the lumen 144.

As shown in FIG. 1B, the cover 180 (which is shown in FIG. 1A) has been removed from the distal end portion 110 of the optical fiber member 100 as represented by the dashed line. The cover 180 can be removed so that electromagnetic radiation C can be emitted from a distal end surface 106 of the waveguide 102. The electromagnetic radiation C can be propagated from within the waveguide 102 from, for example, an electromagnetic radiation source (not shown).

Although not shown, at least a portion of the cover 180 (e.g., the entire cover 180) can be removed (e.g., pulverized) in response to being exposed to electromagnetic radiation (e.g., continuous-wave electromagnetic radiation, pulsed electromagnetic radiation) propagated within the waveguide 102 from an electromagnetic radiation source and incident on the cover 180. In some embodiments, at least a portion of the cover 180 can be removed from the distal end portion 110 of the optical fiber member 100 in response to being, for example, burned by the electromagnetic radiation. In some embodiments, the cover 180 can be removed so that at least the distal surface 106 of waveguide 102 is exposed (e.g., no longer disposed inside of the cover 180). When the distal surface 106 of the waveguide 102 is exposed, electromagnetic radiation from, for example, an electromagnetic radiation source can be propagated within the waveguide 102 and out of the distal surface 106 to a target treatment area of a patient.

In some embodiments, the electromagnetic radiation used to remove the cover 180 can be emitted from an electromagnetic radiation source different from an electromagnetic radiation source used to emit the electromagnetic radiation C. For example, electromagnetic radiation from a first electromagnetic radiation source (not shown) can be propagated within the waveguide 102 so that it is incident on an interior portion of the cover 180. Before such propagation, the interior portion of the cover 180 can be in contact with the distal end surface 106 of the waveguide 102. The electromagnetic radiation from the first electromagnetic radiation source can, for example, burn at least a portion of the cover 180 so that at least the distal end surface 106 of the waveguide 102 is exposed (e.g., no longer disposed inside of the cover 180). After the portion of the cover 180 has been removed using electromagnetic radiation from the first electromagnetic radiation source, the electromagnetic radiation C from a second electromagnetic radiation source can be transmitted through the waveguide 102 and out of the distal surface 106 of the waveguide 102. In some embodiments, the first electromagnetic radiation source can be a cover-removing electromagnetic radiation source and the second electromagnetic radiation source can be used for treatment of a portion (e.g., a tissue) of a body of a patient. In such instances, the first electromagnetic radiation source may not be used to treat the portion of the body of the patient. In some embodiments, electromagnetic radiation from the first electromagnetic radiation source and used for removal of the portion of the cover 180 can be referred to as removal electromagnetic radiation, and the electromagnetic radiation C from the second electromagnetic radiation source and used for treatment of the patient can be referred to as treatment electromagnetic radiation. In some embodiments, treatment electromagnetic radiation (used after removal electromagnetic radiation) can cause some portions of the cover 180 to be removed (e.g., disintegrated).

The cover 180 can be made of any type of material that can be removed (e.g., pulverized) in response to being exposed to, for example, electromagnetic radiation. In some embodiments, the cover 180 can be made from a material that is substantially the same as (e.g., has a composition substantially the same as) a material used to make the jacket 104. In some embodiments, the cover 180 can be made of a material that is opaque (e.g., substantially opaque) to the electromagnetic radiation emitted towards the material to, for example, cause the material to be removed (e.g., disintegrate). In some embodiments, the cover 180 can be made of a material configured to be removed in response to being exposed to electromagnetic radiation from an electromagnetic radiation source for, for example, a second or less (e.g., a few milliseconds). In some embodiments, the cover 180 can be made of a material configured to be removed after more than a second of exposure to electromagnetic radiation from an electromagnetic radiation source. In some embodiments, fragments of the cover 180 that may remain within a body of a patient after being exposed to the electromagnetic radiation source can be removed from the body of the patient with, for example, a basket tool via the endoscopic tube 140 and/or flushed through normal urinary activity.

In some embodiments, the cover 180 can be made of multiple materials that are configured to be removed (e.g., pulverized) from the distal end portion 110 of the optical fiber member 100 at different rates. For example, in some embodiments, the cover 180 can have a first portion (e.g., an inner portion, a side portion, an outer portion) made of a first material configured to be removed (e.g., disintegrate) when exposed to electromagnetic radiation for a first period of time, and the cover 180 can have a second portion (e.g., an inner portion, a side portion, an outer portion) made of a second material configured to be removed (e.g., disintegrate) when exposed to electromagnetic radiation for a second period of time that is longer than the first period of time.

Although not shown, in some embodiments, a cover made of a removable material can be coupled to a different type of optical fiber member other than a straight-fire optical fiber member (such as that shown in FIGS. 1A and 1B). For example, in some embodiments, a cover made of a removable material can be coupled to a side-fire laser fiber member.

Although not shown, in some embodiments, the cover 180 can be disposed only around a portion of the waveguide 102. For example, in some embodiments, the cover 180 can be disposed around, an upper portion of a distal end portion of the waveguide 102 and/or a lower portion of the distal end portion of the waveguide 102 rather than being disposed entirely around the distal end portion of the waveguide 102. In such instances, the cover 180 can have, for example, a semicircular cross-sectional shape when viewed from the distal end.

Figure 2A:
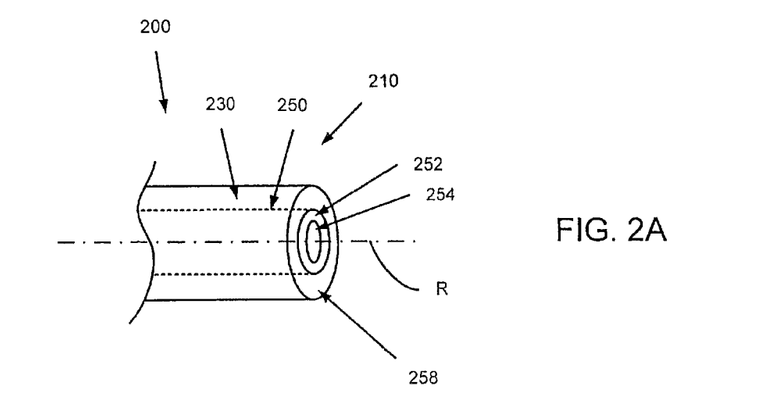
FIG. 2A is a schematic diagram that illustrates a perspective view of a distal end portion of an optical fiber member, according to an embodiment.
Figure 2B:
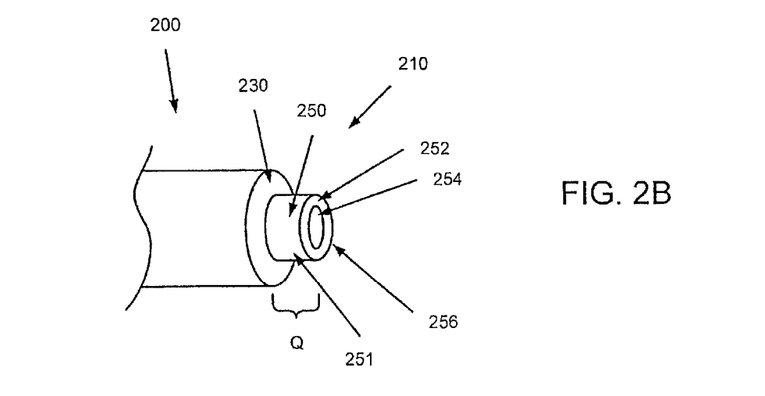
FIG. 2B is a schematic diagram that illustrates a perspective view of the distal end portion of the optical fiber member shown in FIG. 2A after a portion of the jacket has been removed.
Figure 2C:
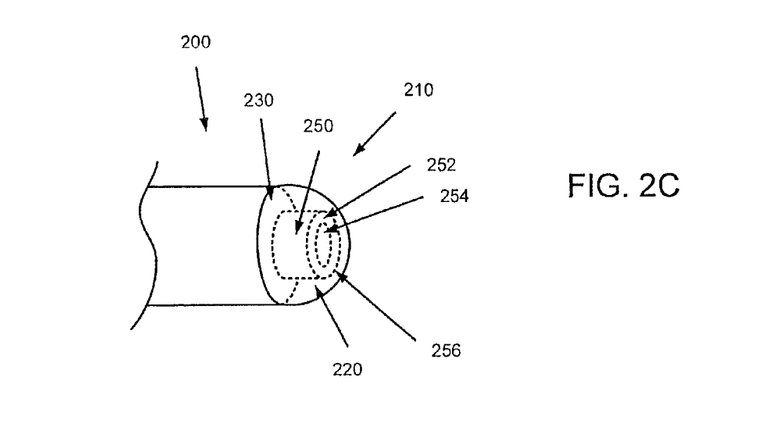
FIG. 2C is a schematic diagram that illustrates a perspective view of the distal end portion of the optical fiber member shown in FIG. 2B after a cover has been coupled to the distal end portion of the optical fiber member.

FIGS. 2A through 2C are schematic diagrams that illustrate a method for disposing (e.g., a coupling) a cover 220 on a waveguide 250 of a distal end portion 210 of an optical fiber member 200, according to an embodiment. In other words, FIGS. 2A through 2C are related to a method for producing a cover 220 for a distal end portion 210 of the optical fiber member 200.

Specifically, FIG. 2A is a schematic diagram that illustrates a perspective view of a distal end portion 210 of an optical fiber member 200, according to an embodiment. As shown in FIG. 2A, the distal end portion 210 of the optical fiber member 200 includes a waveguide 250 and a jacket 230 (e.g., a jacket made of a polymer-based material) disposed axially around the waveguide 250 (e.g., around an outside of a side wall of the waveguide 250). The waveguide 250 includes a cladding layer 252 (e.g., a fluorine-doped cladding layer) and a fiber core 254 (e.g., a substantially pure silica fiber core). In some embodiments, the waveguide 250 can include, for example, another cladding layer (not shown) and/or a buffer layer (not shown) (e.g., an acrylate buffer layer).

As shown in FIG. 2A, the distal end portion 210 of the optical fiber member 200 has a cleaved distal end 258. The cleaved distal end 258 is defined by at least a portion of the cladding layer 252, the fiber core 254, and the jacket 230. In some embodiments, the cleaved distal end 258 can be defined using, for example, a scoring and breaking method and/or a cutting instrument. In some embodiments, the cleaved distal end 258 can be substantially flat and/or polished. In some embodiments, a longitudinal axis or centerline R of the distal end portion 210 of the optical fiber member 200 can be substantially normal to a plane defined by the cleaved distal end 258.

FIG. 2B is a schematic diagram that illustrates a perspective view of the distal end portion 210 of the optical fiber member 200 shown in FIG. 2A after a portion of the jacket 230 has been removed. As shown in FIG. 2B, the portion of the jacket 230 has been stripped from the distal end portion 210 to expose at least a portion of a side wall 251 (also can be referred to as an axial portion) of the cladding layer 252 of the waveguide 250 of the optical fiber member 200. The portion of the side wall of the cladding layer 252 that is exposed has a length Q. Although not shown, in some embodiments, the cladding layer 252 can be chemically and/or mechanically stripped to, for example, expose at least a portion of a side wall of the fiber core 254.

As shown in FIG. 2B, an edge 256 of the waveguide 250 is exposed when the portion of the jacket 230 has been stripped from the distal end portion 210 of the optical fiber member 200. If inserted into, for example, a lumen defined by an endoscopic tube (not shown), the edge 256 of the waveguide 250 could snag within and/or cut an inner portion of the endoscopic tube.

FIG. 2C is a schematic diagram that illustrates a perspective view of the distal end portion 210 of the optical fiber member 200 shown in FIG. 2B after a cover 220 has been coupled to the distal end portion 210 of the optical fiber member 200. As shown in FIG. 2C, the edge 256 of the waveguide 250 is covered by the cover 220 and the cover 220 is coupled to the jacket 230 of the distal end portion 210 of the optical fiber member 200.

In some embodiments, the cover 220 shown in FIG. 2C can be defined, at least in part, by depositing a material onto the waveguide 250. In some embodiments, the cover 220 can be made, at least in part, from a component formed from a material separate from the optical fiber member 200, and can be coupled to (e.g., press-fit onto, melted onto, coupled using an adhesive) the waveguide 250. Although not shown, in some embodiments, at least a portion of the cover 220 can be coupled to (e.g., disposed on) an axial portion (e.g., an outer surface of a side wall) of the jacket 230.

In some embodiments, the shape of the cover 220 shown in FIG. 2C can be defined after a material (e.g., a component made from the material) has been initially coupled to the distal end portion 210 of the optical fiber member 200. For example, a component with distal edges and/or proximal edges (e.g., a square component) made from a removable material can be coupled to the distal end portion 210 of the optical fiber member 200. The distal and/or proximal edges of the component can be polished and/or heated (e.g., melted by heat) so that the shape of the cover 220 shown in FIG. 2C is defined. In some embodiments, the shape of the cover 220 can be different than the conical shape shown in FIG. 2C. More details related to removable covers of various shapes are described in connection with FIGS. 6 through 9.

In some embodiments, the cover 220 can be formed using a dipping process. For example, after the portion of the jacket 230 has been stripped (as shown in FIG. 2B) the distal end portion 210 of the optical fiber member 200 can be dipped into a material (e.g., a material in a melted state). In some embodiments, the cover 220 can be formed using a deposition process. For example, after the portion of the jacket 230 has been stripped (as shown in FIG. 2B) a material can be deposited onto the distal end portion 210 of the optical fiber member 200 using a deposition process. The material can be configured to adhere (e.g., bond to, stick to) to the distal end portion 210 of the optical fiber member 200 (using the dipping process and/or the deposition process). In some embodiments, the material that has adhered to the distal end portion 210 of the optical fiber member 200 can be processed, if necessary, to define the shape of the cover 220.

Figure 3A:
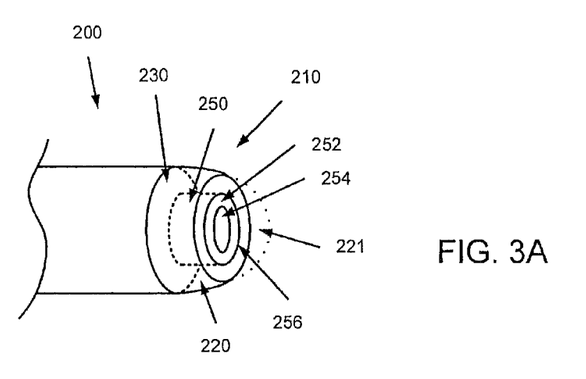
FIG. 3A is a schematic diagram that illustrates a perspective view of the distal end portion of the optical fiber member after at least a portion of the cover shown in FIG. 2C is removed, according to an embodiment.
Figure 3B:
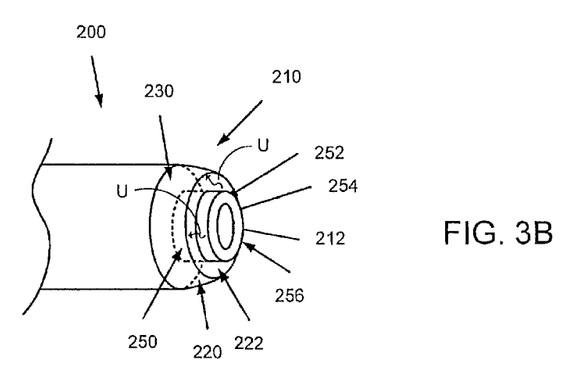
FIG. 3B is a schematic diagram that illustrates a perspective view of a distal surface of the cover after a portion of the cover is removed in response to reflected electromagnetic radiation.

FIGS. 3A and 3B are schematic diagrams that illustrate the distal end portion 210 of the optical fiber member 200 during portions (e.g., phases) of a medical procedure after the cover 220 has been coupled to the distal end portion 210 of the optical fiber member 200 (as shown in FIGS. 2A through 2C). In other words, FIGS. 3A and 3B are related to use of the distal end portion 210 of the optical fiber member 200 after the cover 220 has been coupled to the distal end portion 210 of the optical fiber member 200.

Specifically, FIG. 3A is a schematic diagram that illustrates a perspective view of the distal end portion 210 of the optical fiber member 200 after at least a portion 221 of the cover 220 shown in FIG. 2C is removed, according to an embodiment. As shown in FIG. 3A, the portion 221 of the cover 220 that is removed is represented by a dotted line. In some embodiments, the portion 221 of the cover 220 can be removed during a removal portion of a medical procedure. Specifically, the portion 221 of the cover 220 can be removed in response to being exposed to electromagnetic radiation from an electromagnetic radiation source (not shown). In some embodiments, the portion 221 of the cover 220 can be removed after the distal end portion 210 of the optical fiber member 200 has been placed in a desirable position with respect to a treatment area of a patient.

In some embodiments, the electromagnetic radiation can be defined by the electromagnetic radiation source to specifically remove the portion 221 of the cover 220. In other words, one or more characteristics of the electromagnetic radiation can be defined for removal of the portion 221 of the cover 220. For example, the electromagnetic radiation can be propagated within at least a portion of the waveguide 250 so that the electromagnetic radiation is incident on the portion 221 of the cover 220 (e.g., an interior portion of the cover 220) for a specified duration(s), in a pulsed fashion, at a specified power level, within a specified range of wavelengths of electromagnetic radiation, and so forth. In some embodiments, one or more characteristics of electromagnetic radiation used for removal of the portion 221 of the cover 220 can be different than one or more characteristics of electromagnetic radiation used for treatment of a patient after the portion 221 of the cover 220 has been removed. In some embodiments, electromagnetic radiation used for removal of the portion 221 of the cover 220 can be referred to as removal electromagnetic radiation and electromagnetic radiation used for treatment of a patient after the portion 221 of the cover 220 has been removed can be referred to as treatment electromagnetic radiation. Although not shown, in some embodiments, the electromagnetic radiation used for removal of the portion 221 of the cover 220 can be produced by an electromagnetic radiation source different from an electromagnetic radiation source used during treatment of a patient after the portion 221 of the cover 220 has been removed.

FIG. 3B is a schematic diagram that illustrates a perspective view of a distal surface 222 of the cover 220 after a portion of the cover 220 is removed in response to reflected electromagnetic radiation U. As shown in FIG. 3B, a portion of a distal surface 222 of the cover 220 is exposed in response to electromagnetic radiation U reflected from at least a portion of a surface 212 defined by the waveguide 250 and incident on the cover 220 causing a portion of the cover 220 to be removed. Specifically, portions of the cover 220 can be, for example, burned back by the electromagnetic radiation U so that the distal surface 222 of the cover 220 is exposed. In some embodiments, the distal surface 222 of the cover 220 can be exposed in response to the reflected electromagnetic radiation U during a removal portion of a medical procedure and/or during a treatment portion of a medical procedure. In other words, the electromagnetic radiation U can be removal electromagnetic radiation and/or treatment electromagnetic radiation.

Figure 4:
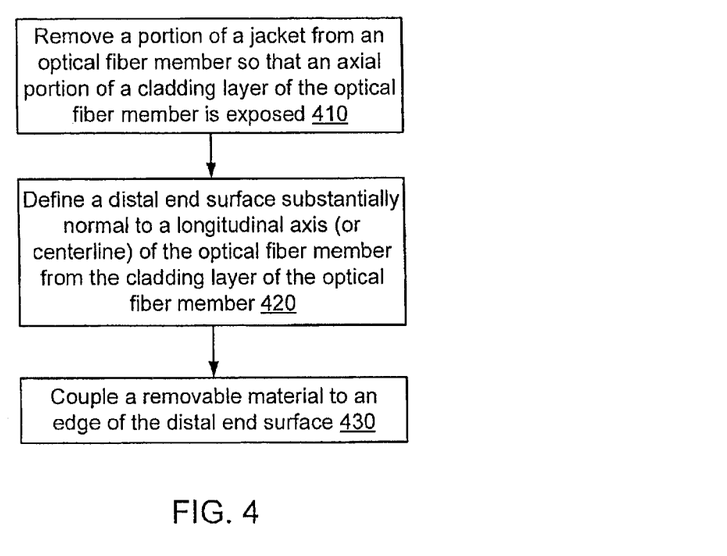
FIG. 4 is a flowchart that illustrates a method for coupling a cover made of a removable material to a distal end portion of an optical fiber member, according to an embodiment.

FIG. 4 is a flowchart that illustrates a method for coupling a cover made of a removable material to a distal end portion of an optical fiber member, according to an embodiment. As shown in FIG. 4, a portion of a jacket is removed from an optical fiber member so that an axial portion of a cladding layer of the optical fiber member is exposed, at 410.

A distal end surface substantially normal to a longitudinal axis (or centerline) of the optical fiber member is defined from the cladding layer of the optical fiber member, at 420. The distal end surface of the cladding layer can be co-planar with a distal end surface of a fiber core of the optical fiber member. In some embodiments, the distal end surface can be, for example, polished. In some embodiments, removing the portion of the jacket from the optical fiber member (shown in block 410) may be performed to facilitate the defining of the distal end surface.

A removable material is coupled to an edge of the distal end surface, at 430. In some embodiments, the removable material can be coupled on or around the edge of the distal end surface. In some embodiments, the removable material can be coupled so that the edge of the distal end surface may not be exposed in an undesirable fashion during a placement portion of a medical procedure. In some embodiments, the coupling of the removable material can include, for example, disposing, depositing, dipping, and/or so forth.

In some embodiments, the removable material can be made of a material that is substantially similar to that of the jacket. In some embodiments, the removable material can be made a material that is different from that of the jacket.

In some embodiments, removing a portion of a jacket (shown in block 410) may be optional. In other words, the defining shown in block 420 and/or the coupling shown in block 430 may be performed without stripping a portion of the jacket from the optical fiber member. In such instances, the jacket may be substantially co-extensive with at least a portion of the distal end surface of a waveguide (e.g., a fiber core of the optical waveguide) of the optical fiber member.

Figure 5:
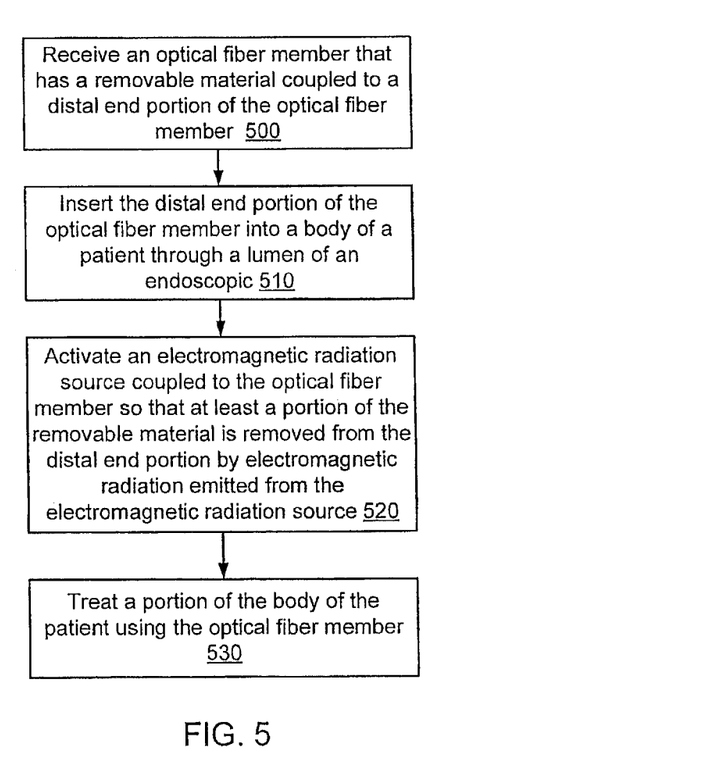
FIG. 5 is a flowchart that illustrates a method for using a distal end portion of an optical fiber member that has a cover made of a removable material, according to an embodiment.

FIG. 5 is a flowchart that illustrates a method for using a distal end portion of an optical fiber member that has a cover made of a removable material, according to an embodiment. As shown in FIG. 5, an optical fiber member that has a removable material coupled to a distal end portion of the optical fiber member is received, at 500. In some embodiments, the removable material can be coupled to the distal end portion of the optical fiber member using the method described in connection with FIG. 4.

The distal end portion of the optical fiber member is inserted into a body of a patient through a lumen of an endoscope, at 510. The removable material defines a cover that can facilitate movement of the optical fiber member within the lumen of an endoscope (e.g., an endoscopic tube) without damaging the optical fiber member and/or the lumen of an endoscope. In some embodiments, the distal end portion of the optical fiber member can be inserted into the body of the patient during a placement portion of a medical procedure.

An electromagnetic radiation source coupled to the optical fiber member is activated so that at least a portion of the removable material is removed from the distal end portion by electromagnetic radiation emitted from the electromagnetic radiation source, at 520. In some embodiments, the electromagnetic radiation can be propagated within a waveguide of the optical fiber member so that the electromagnetic radiation collides with the portion of the removable material and, for example, fragments the removable material.

In some embodiments, the portion of the removable material can be removed during a removal portion of a medical procedure. In some embodiments, the portion of the removable material can be removed when the distal end portion is disposed outside a distal end of the endoscopic tube or within a portion of the endoscopic tube. In some embodiments, the portion of the removable material can be removed while the distal end portion of the optical fiber member is being inserted into the body of the patient as described in connection with block 510.

A portion of the body of the patient is treated using the optical fiber member, at 530. In some embodiments, the portion of the body of the patient can be treated using electromagnetic radiation emitted from the electromagnetic radiation source described in connection with block 520 and/or a different electromagnetic radiation source. In some embodiments, the portion of the body of the patient can be treated during a treatment portion of a medical procedure.

Figure 6:
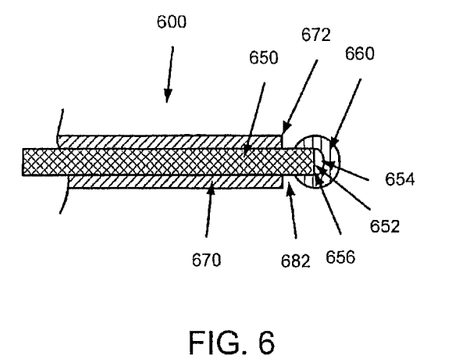
FIG. 6 is a schematic diagram of a side cross-sectional view of a removable cover coupled to an optical fiber member, according to an embodiment.

FIG. 6 is a schematic diagram of a side cross-sectional view of a removable cover 660 coupled to an optical fiber member 600, according to an embodiment. The optical fiber member 600 has a waveguide 650 and a jacket 670. As shown in FIG. 6, the removable cover 660 has a substantially spherical shape and is disposed around an edge 656 of the waveguide 650. As shown in FIG. 6, the removable cover 660 is coupled to the waveguide 650 such that a portion 682 of the waveguide 650 is exposed after the removable cover 660 has been coupled to the waveguide 650. Accordingly, a proximal end of the removable cover 660 is not in contact with the jacket 670.

As shown in FIG. 6, a cavity 654 is disposed between a distal end surface 652 of the waveguide 650 and an interior portion of the removable cover 660. Although not shown, in some embodiments, the removable cover 660 can be defined so that the cavity 654 is not disposed between the distal end surface 652 of the waveguide 650 and the removable cover 660. In such instances, substantially an entire interior portion of the removable cover 660 can be coupled to the waveguide 650 (e.g., coupled to waveguide 650 without any remaining space or cavity).

In some embodiments, a cover (not shown) that is different from the cover 660 can be coupled to the jacket 670 so that an edge 672 of the jacket 670 may not, for example, snag an interior portion of an endoscopic tube (not shown). In some embodiments, the cover coupled to the jacket 670 can be coupled to or can be separate and spaced apart from the cover 660. The cover coupled to the jacket 670 mayor may not be a made of a material configured to be removed in response to incident electromagnetic radiation.

Although not shown, in some embodiments, a cover can be coupled to a distal end portion of an optical fiber member 600 such that the cover is coupled only to the jacket 670 (e.g., an outer surface of a side wall of the jacket 670, a distal end surface of the jacket 670) of the optical fiber member 600. In such instances, an interior portion of the cover may not contact any portion of the waveguide 650. In other words, a cover can be coupled to the jacket 670 (e.g., an outer surface of a side wall of the jacket 670 and/or a distal end surface of the jacket 670) and/or at least a portion of the waveguide 650 (e.g., an outer surface of a side wall of the waveguide 650 and/or the distal end surface 652 of the waveguide 650).

Figure 7:
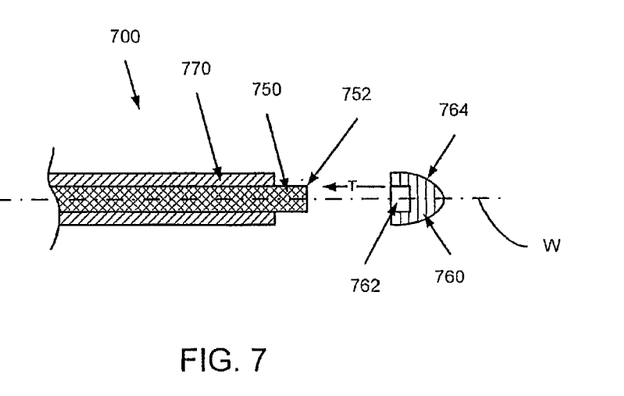
FIG. 7 is a schematic diagram of a side cross-sectional view of a removable cover being coupled to an optical fiber member, according to an embodiment.

FIG. 7 is a schematic diagram of a side cross-sectional view of a removable cover 760 being coupled to an optical fiber member 700, according to another embodiment. The optical fiber member 700 has a waveguide 750 and a jacket 770. At least a portion of the jacket 770 has been stripped from the waveguide 750 to expose a distal end portion of the waveguide 750. As shown in FIG. 7, an arc of curvature 764 on an outer surface of the cover 760 can be co-planar with a longitudinal axis (or centerline) W of the cover 760 and/or the optical fiber member 700.

As shown in FIG. 7, the removable cover 760 can be moved in direction T so that a cavity 762 defined by the removable cover 760 can be placed over the edge 752 of the waveguide 750. In some embodiments, the cavity 762 of the removable cover 760 can be defined so that the removable cover 760 can be press fit to the waveguide 750 over the edge 752. In some embodiments, the removable cover 760 can be heated so that the removable cover 760 is substantially fixedly coupled to the distal end portion of the waveguide 750 and/or the jacket 770. In some embodiments, a proximal end of the removable cover 760 mayor may not be coupled to the jacket 770.

Figure 8:
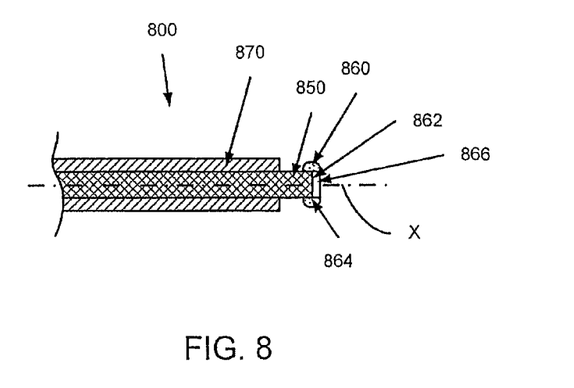
FIG. 8 is a schematic diagram of a side cross-sectional view of a removable cover coupled to an optical fiber member, according to another embodiment.

FIG. 8 is a schematic diagram of a side cross-sectional view of a removable cover 860 coupled to an optical fiber member 800, according to another embodiment. The optical fiber member 800 has a waveguide 850 and a jacket 870. At least a portion of the jacket 870 has been stripped from the waveguide 850, and the removable cover 860, which has toroid shape, is coupled to the waveguide 850 around an edge 864 of the waveguide. As shown in FIG. 8, an opening 866 defined by the removable cover 860 is aligned along a plane that is substantially normal to a longitudinal axis (or centerline) X of the waveguide 850 so that a distal end surface 862 of the waveguide 850 is exposed through the opening 866. Although not shown, in some embodiments, the removable cover 860 can have an opening (not shown) that is not aligned along a plane normal to the longitudinal axis (or centerline) X of the waveguide 850.

In some embodiments, portions of the removable cover 860 can be removed in response to electromagnetic radiation being propagated within the waveguide 850. In some embodiments, portions of the removable cover 860 can be removed in response to electromagnetic radiation being reflected from a proximal side of the distal end surface 862 of the waveguide 850.

Figure 9:
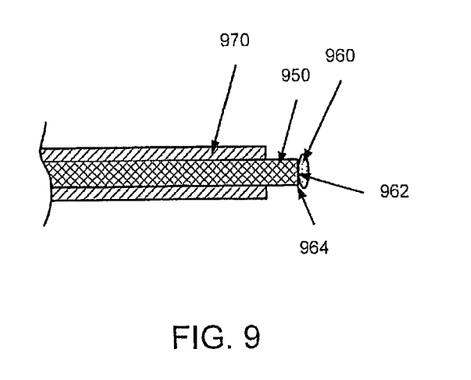
FIG. 9 is a schematic diagram of a side cross-sectional view of a removable cover coupled to an optical fiber member, according to yet another embodiment.

FIG. 9 is a schematic diagram of a side cross-sectional view of a removable cover 960 coupled to an optical fiber member 900, according to yet another embodiment. The optical fiber member 900 has a waveguide 950 and a jacket 970. At least a portion of the jacket 970 has been stripped from the waveguide 950 and the removable cover 960 is coupled to a distal end surface 962 of the waveguide 950. As shown in FIG. 9, the removable cover 960 is not disposed around an edge 964 of the waveguide 950. The removable cover 960 has a size sufficient to substantially prevent the edge 964 of the waveguide 950 from coming in contact with, for example, a inner portion of an endoscopic tube (not shown) during a placement portion of a medical procedure.

In some embodiments, the removable cover 960 can be coupled to the distal end surface 962 of the waveguide 950 using, for example, an adhesive. In some embodiments, removable cover 960 can be placed on the distal end surface 962 of the waveguide 950 and can be heated so that the removable cover 960 adheres to the distal end surface 962 of the waveguide 950.

While various embodiments have been described above, it should be understood that they have been presented by way of example only, not limitation, and various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described. For example, multiple different types of removable covers can be coupled to a single optical fiber member. In some embodiments multiple different electromagnetic radiation sources can be used to remove a cover.

Other embodiments will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. An apparatus, comprising:
    a waveguide having a distal end surface substantially normal to a centerline of a distal end portion of the waveguide;
    a selectively removable cover coupled to a distal end portion of the waveguide, wherein the selectively removable cover is made of a material configured to be removed when exposed to electromagnetic radiation emitted from a portion of the distal end surface of the waveguide; and
    a jacket disposed around the waveguide, wherein the cover includes a proximal end separated from a distal end of the jacket by an air gap;
    wherein the cover includes a substantially spherical shape disposed around an edge of the waveguide and spaced from the jacket.

2. The apparatus of claim 1, wherein the cover and the waveguide are positioned so as to form a cavity between the distal end surface of the waveguide and an interior portion of the cover.

3. The apparatus of claim 1, wherein the cover is a first cover, the apparatus further comprising:
    a second cover, different from the first cover, the second cover being coupled to the jacket.

4. The apparatus of claim 3, wherein the second cover is coupled to the first cover.

5. The apparatus of claim 3, wherein the second cover is made of a material configured to be removed when exposed to electromagnetic radiation emitted from the portion of the distal end surface of the waveguide.

6. The apparatus of claim 1, wherein the material is substantially opaque to the electromagnetic radiation when emitted from the distal end surface of the waveguide.

7. The apparatus of claim 1, wherein the selectively removable cover is made of a plurality of materials configured to be removed when exposed to electromagnetic radiation emitted from a portion of the distal end surface of the waveguide, and wherein a first material of the plurality of materials is configured to be removed at a rate different than a rate of removal of a second material of the plurality of materials.

8. The apparatus of claim 1, wherein the material is configured to be removed by at least one of pulverizing and melting when exposed to electromagnetic radiation emitted from a portion of the distal end surface of the waveguide.

9. The apparatus of claim 1, wherein the distal end surface of the waveguide is defined partially by a fiber core of the waveguide.

10. The apparatus of claim 1, wherein the cover is adhesively coupled to at least one of a cladding layer of the waveguide and the edge of the waveguide.

11. The apparatus of claim 1, wherein the waveguide is included in a ureteroscope.

12. An apparatus, comprising:
   a waveguide having a distal end surface substantially normal to a centerline of a distal end portion of the waveguide;
   a selectively removable spherical cover coupled to a distal end portion of the waveguide, wherein the selectively removable cover is made of a material configured to be removed when exposed to electromagnetic radiation emitted from a portion of the distal end surface of the waveguide; and
   wherein the cover and the waveguide are positioned so as to form a cavity between the distal end surface of the waveguide and an interior portion of the cover.

13. The apparatus of claim 12, wherein the material is substantially opaque to the electromagnetic radiation when emitted from the distal end surface of the waveguide.

14. The apparatus of claim 12, wherein the selectively removable cover is made of a plurality of materials configured to be removed when exposed to electromagnetic radiation emitted from a portion of the distal end surface of the waveguide, and wherein a first material of the plurality of materials is configured to be removed at a rate different than a rate of removal of a second material of the plurality of materials.

15. The apparatus of claim 12, wherein the material is configured to be removed by at least one of pulverizing and melting when exposed to electromagnetic radiation emitted from a portion of the distal end surface of the waveguide.

16. The apparatus of claim 12, wherein the distal end surface of the waveguide is defined partially by a fiber core of the waveguide.

17. The apparatus of claim 12, wherein the cover is adhesively coupled to at least one of a cladding layer of the waveguide and an edge of the waveguide.

18. A method, comprising:
   inserting a distal end portion of a waveguide into a body of a patient through an endoscopic tube, wherein the waveguide includes a removable spherical cover coupled to a distal end surface of the distal end portion of the waveguide, and the distal end surface is substantially normal to a centerline of the distal end portion of the waveguide; and
   activating an electromagnetic radiation source coupled to a proximal end portion of the waveguide such that a portion of the removable cover is removed from the distal end surface by electromagnetic radiation emitted from the electromagnetic radiation source;
   wherein the cover and the waveguide are positioned so as to form a cavity between the distal end surface of the waveguide and an interior portion of the cover.

19. The method of claim 18, wherein the removable material is configured such that the portion of the removable material is removed within one second of the activating.

20. The method of claim 18, wherein the removable cover is made of a plurality of materials configured to be removed when exposed to electromagnetic radiation emitted from a portion of the distal end surface of the waveguide, and wherein a first material of the plurality of materials is configured to be removed at a rate different than a rate of removal of a second material of the plurality of materials.

* * * * *